United States Patent [19]

Monbaliu et al.

[11] 4,130,427

[45] Dec. 19, 1978

[54] SILVER HALIDE EMULSION CONTAINING TWO-EQUIVALENT COLOR COUPLERS FOR YELLOW

[75] Inventors: Marcel J. Monbaliu, Mortsel; Räphael K. Van Poucke, Berchem, both of Belgium

[73] Assignee: Agfa-Gevaert, N.V., Mortsel, Belgium

[21] Appl. No.: 802,053

[22] Filed: May 31, 1977

[30] Foreign Application Priority Data

Jun. 9, 1976 [GB] United Kingdom ............... 23917/76

[51] Int. Cl.$^2$ ............................ G03C 7/00; G03C 1/40
[52] U.S. Cl. ..................... 96/56.5; 96/100 R
[58] Field of Search ............... 96/100, 56.5, 56

[56] References Cited

U.S. PATENT DOCUMENTS

| 2,435,550 | 2/1948 | Bauley | 96/56.5 |
| 3,227,550 | 1/1966 | Whitmore et al. | 96/100 |
| 3,839,044 | 10/1974 | Salminen et al. | 96/100 |

*Primary Examiner*—J. Travis Brown
*Attorney, Agent, or Firm*—A. W. Breiner

[57] ABSTRACT

2-equivalent color couplers for yellow carrying at the coupling position via an oxygen atom a 5-membered N-containing unsaturated heterocyclic substituent, that is split off during oxidative coupling with an aromatic primary amine color developer and forms a competing coupler molecule.

5 Claims, No Drawings

SILVER HALIDE EMULSION CONTAINING TWO-EQUIVALENT COLOR COUPLERS FOR YELLOW

The present invention relates to novel 2-equivalent yellow forming colour couplers and to their use for the production of photographic colour images.

It is known that for the production of a photographic colour image in a light-sensitive silver halide layer, the co-exposed silver halide is developed to a silver image by means of an aromatic primary amino compound in the presence of a colour coupler, which reacts with the oxidized developing substance to form a dyestuff image corresponding to the silver image.

In the subtractive three-colour photography a light-sensitive photographic colour material is used containing red-sensitized, green-sensitized and blue-sensitive silver halide emulsion layers wherein on colour development cyan, magenta and yellow dyestuff images are formed respectively by coupling of appropriate colour couplers with an oxidized aromatic primary amino colour developing agent.

It is common practice to use for the formation of the cyan dye image phenol or naphthol colour couplers, for the formation of the magenta dye image 2-pyrazolin-5-one colour couplers and for the formation of the yellow dye image ketomethylene couplers containing a methylene group having two carbonyl groups attached to it.

It is also known to employ besides colour couplers wherein the coupling position is unsubstituted, thus requiring for the formation of one molecule of dyestuff the development of 4 molecules of exposed silver halide, colour couplers wherein the coupling position carries a substituent that is split off upon colour development so that only two exposed silver halide molecules should be developed to form one molecule of dyestuff. The former compounds are known as 4-equivalent couplers whereas the latter are known as 2-equivalent couplers.

Groups particularly suitable for being split off at the coupling position from 2-equivalent colour couplers are halogen atoms e.g. chlorine, alkoxy groups, aryloxy groups, alkylthio groups, arylthio groups and a variety of heterocyclic groups e.g. as described in the published German Patent Application Nos. 2,057,941; 2,163,812; 2,213,461; 2,318,807; 2,329,587; 2,363,675; 2,414,006 and 2,433,812.

The principal advantages of 2-equivalent colour couplers are known. They require approximately half as much silver halide as the 4-equivalent couplers so that in the preparation of the silver halide elements less silver halide can be used and thinner emulsion layers can be employed, which results in improved resolution, improved sharpness, and a better transparency for light through the successive emulsion layers resulting in improved speed. Some groups which are split off inhibit development and couplers containing such groups are known as D.I.R.-couplers (Development Inhibitor Releasing Couplers) or I.C.C.-couplers (Interlayer Colour Correction Couplers).

However, 2-equivalent colour couplers may pose various problems, e.g. too low a coupling activity, increased fog in developed areas of the photographic element, where the silver halide is not exposed and colour distortions e.g. too low a maximum colour density, unfavourable spectral absorption characteristics and unstability against light, heat and humidity of the dyes formed. Increased fog upon storing is particularly pronounced with 2-equivalent yellow-forming colour couplers.

According to the published German Pat. No. 2,420,067 photographic materials comprising 2-equivalent yellow-forming colour couplers have improved properties especially reduced fog when the blue-sensitive silver halide emulsion layer contains in addition to the 2-equivalent yellow forming colour coupler a colourless coupling component (competing coupler), particularly a 4-monoalkyl-substituted 2-pyrazolin-5-one coupler.

Competing couplers are well known for use in photographic colour elements. They react with the oxidation products of the developing agent to form colourless compounds and are used in those instances where undesirable oxidation products of the developing agent should be rendered ineffective so that degradation of the image quality is inhibited.

In the Belgian Pat. No. 843,896 2-equivalent colour couplers, more particularly 2-equivalent open chain ketomethylene colour couplers for yellow, are described having high coupling activity and improved photographic properties, especially reduced fog formation. These 2 equivalent colour couplers carry as substituents at the coupling position a 5-membered nitrogen-containing unsaturated heterocyclic ring, which splits off upon colour coupling, wherein the split off heterocycle is capable of coupling with the oxidation products of aromatic primary amino colour developing agents to form colourless compounds, more particularly a 4-monoalkyl-3-pyrazolin-5-one group, which is linked to the coupling position of the coupler through its nitrogen atom in the 2-position.

The present invention provides novel 2-equivalent open chain ketomethylene colour couplers for yellow and carry at the coupling position a 5-membered nitrogen-containing unsaturated heterocyclic substituent that is split off during oxidative coupling with an aromatic primary amino colour developer and forms a competing coupler molecule which is capable of coupling with the oxidation products of an aromatic primary amino colour developer to form a colourless compound characterized in that the heterocyclic substituent is a 5-pyrazolyl-oxy substituent which when split off forms a 1-aryl- or 1-alkyl-4-monoalkyl-2-pyrazolin-5-one competing coupler compound. The present invention also provides photographic colour elements containing such 2-equivalent colour couplers and processes of forming photographic colour images by development of exposed silver halide elements by means of aromatic primary amino colour developing agents in the presence of such colour couplers.

The novel 2-equivalent colour couplers of the present invention have high coupling activity, produce little fog and produce upon colour development yellow dyes of improved light stability as compared with the corresponding 4-equivalent couplers and other 2-equivalent couplers.

The 1-alkyl and 1-aryl groups of the 5-pyrazolyloxy substituent may carry any of the substituents normally provided in 1-alkyl and 1-aryl groups of 2-pyrazolin-5-one couplers. Thus the 1-substituent may be a $C_1$–$C_{12}$ alkyl group, especially $C_1$–$C_5$ alkyl, which may be substituted e.g. with halogen, cyano or phenyl such as 2,2,2-trifluoroethyl, cyanoethyl, benzyl, chlorobenzyl and the like, or an aryl group e.g. phenyl which may carry one or more substituents such as alkyl e.g. methyl, halogen, e.g. chlorine and bromine, sulpho, alkoxy e.g. methoxy, phenoxy, alkyl sulphonyl e.g. methyl sulphonyl, alkylthio, e.g. methylthio, carbalkoxy, haloalkoxy, haloalkylthio, haloalkylsulphonyl, sulphamoyl, carbamoyl, cyano, nitro.

The 3-position of the 5-pyrazolyl-oxy substituent may carry any of the substituents normally provided in 2-pyrazolin-5-one coupler compounds, which include e.g. alkyl, aryl, substituted alkyl, substituted aryl, carboxyl, alkoxycarbonyl, amino and substituted amino e.g. anilino, substituted anilino, acylamino and substituted acylamino.

The 2-equivalent colour couplers for yellow of the present invention can be represented more particularly by the following formula:

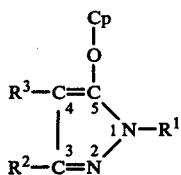
I wherein Cp represents an open chain ketomethylene yellow forming colour coupler residue capable of oxidative coupling with an aromatic primary amino developing agent and linked to the 5-pyrazolyloxy group at its active methylene coupling position;

$R^1$ represents a substituent of the type customarily used in the 1-position of 2-pyrazolin-5-one colour couplers, preferably a $C_1-C_{22}$ alkyl group, especially $C_1-C_5$ alkyl, which may be substituted, e.g. with halogen, cyano, or phenyl, such as 2,2,2-trifluoroethyl, cyanoethyl, benzyl, chlorobenzyl and the like, or an aryl group e.g. phenyl, which may carry one or more substituents such as alkyl e.g. methyl, halogen (e.g. chlorine and bromine), sulpho, alkoxy (e.g. methoxy), phenoxy, alkylsulphonyl (e.g. methylsulphonyl), alkylthio (e.g. methylthio), carbalkoxy, haloalkoxy, haloalkylthio, haloalkylsulphonyl, sulphamoyl, carbamoyl, cyano, nitro;

$R^2$ a substituent of the type commonly present in the 3-position of 2-pyrazolin-5-one couplers e.g. alkyl, substituted alkyl, aryl, substituted aryl, carboxyl, alkoxycarbonyl, amino and substituted amino e.g. anilino, substituted anilino, acylamino and substituted acylamino;

$R^3$ an alkyl group e.g. $C_1-C_5$ alkyl group or substituted alkyl group, or $R^2$ and $R^3$ can represent together a tri- or tetramethylene group thus forming with the carbon atoms to which they are attached a 5- or 6-membered carbocyclic ring.

The effectiveness of the colour couplers of the invention as 2-equivalent couplers is not dependent on the specific composition of the coupler moiety Cp and it will be understood that this moiety may be varied widely to meet such requirements as spectral absorptivity, reactivity, diffusibility or nondiffusibility etc. as may be imposed by the photographic system in which the couplers are to be used.

The present invention is particularly concerned with 2-equivalent yellow-forming colour couplers of the above general formula I wherein Cp stands for a residue of the following general formula II:

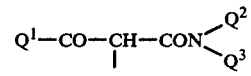
II.

wherein:

each of $Q^1$ and $Q^3$ represents an aliphatic, aromatic or heterocyclic group, and $Q^2$ represents hydrogen or a $C_1-C_5$ alkyl group e.g. methyl.

Representative groups for $Q^1$ are a straight-chain or branched-chain alkyl group, preferably comprising from 1 to 18 C-atoms, which in the case of a secondary or tertiary alkyl group is preferably linked to the carbonyl group by means of the secondary or tertiary carbon atoms, an alkoxyalkyl group, a dicycloalkyl group, a heterocyclic or an aryl group, preferably a phenyl group which may carry one or more substituents: e.g. $C_1-C_{18}$ alkyl, $C_1-C_{18}$ alkoxy, aralkyl, aryl, aroxy, sulpho, carboxy, halogen e.g. chlorine, bromine and fluorine, hydroxy, nitro, cyano, acyl, acyloxy, acylamino, sulphonamido, amino, carbamoyl or sulphamoyl; these substituents may further be substituted by alkyl, aryl, aralkyl or a heterocycle.

Representative groups for $Q^3$ are $C_1-C_{18}$ alkyl, a heterocycle e.g. a 2-thiazolyl group or, preferably aryl e.g. phenyl which may be substituted by one or more substituents: e.g. $C_1-C_{18}$ alkyl, $C_1-C_{18}$ alkoxy, halogen, e.g. chlorine, bromine and fluorine, hydroxy, nitro, cyano, sulpho, carboxy, aryl, aralkyl, aroxy, acyl, acyloxy, acylamino, sulphonamido, amino, carbamoyl or sulphamoyl groups which may be further substituted by alkyl, aryl, aralkyl or a heterocycle.

The 2-equivalent colour couplers according to the present invention are naturally preferably derived from corresponding 4-equivalent couplers having excellent properties as regards the absorption characteristics and stability of the dyes formed upon colour development. Preferred yellow-forming colour couplers are pivaloylacetanilides and benzoylacetanilides, more particularly those corresponding to the above formula I and II wherein Cp represents one of the formulae III and IV:

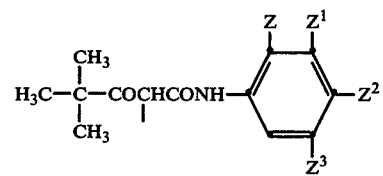
III.

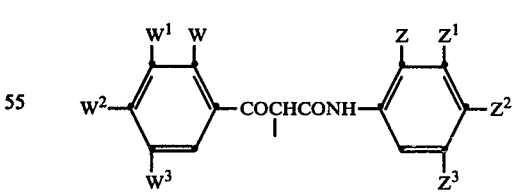
IV.

wherein:

Z represents halogen e.g. fluorine, chlorine or bromine, alkyl e.g. methyl or ethyl, alkoxy e.g. methoxy, ethoxy or hexadecyloxy, aryloxy e.g. phenoxy or methylphenoxy, or N-substituted amino e.g. N,N-dimethylamino, each of $Z^1$, $Z^2$ and $Z^3$, which may be the same or different, represents hydrogen, halogen e.g. fluorine, chlorine or bromine, alkyl e.g. methyl, ethyl or hexadecyl, alkoxy e.g. methoxy, ethoxy or hexadecyloxy, aryl e.g. phenyl or tolyl, aryloxy e.g. phenoxy or methylphenoxy, alkoxycarbonyl e.g. methoxycarbonyl, ethoxycarbonyl or dodecyloxycarbonyl, aryloxycarbonyl, alkylsulphonyl e.g. methylsulphonyl or hexadecylsulphonyl, carbamoyl e.g. methylcarbamoyl, N-t-butylcarbamoyl, dodecylcarbamoyl, N-methyl-N-hexadecylcarbamoyl, or dimethylcarbamoyl, sulphamoyl e.g. methylsulphamoyl, dimethylsulphamoyl, N-methyl-N-hexadecylsulphamoyl, or N-(2,4-di-t-amyl phenoxy)-propyl-sulphamoyl, amino or substituted amino e.g. alkylamino, arylamino and acylamino e.g. N,N-dimethylamino or N-methyl-N-hexadecylamino, anilino, acetamino, acrylamino, methacrylamino, a phenoxy butyramino e.g. 2,4-di-t-amylphenoxy butyramino or ethoxycarbonylamino, an ureido group, a sulpho group or carboxy group in acid or salt form, or a hydroxy group, and each of W, $W^1$, $W^2$ and $W^3$, which may be the same or different represents hydrogen, alkyl e.g. methyl, ethyl or t-butyl, alkoxy, e.g. methoxy, ethoxy or hexadecyloxy, halogen e.g. fluorine, bromine or chlorine, aryloxy e.g. phenoxy or methylphenoxy, amino and substituted amino e.g. alkylamino, aryl and acylamino e.g. N,N-dimethylamino or N-methyl-N-hexadecylamino or an acylamino group e.g. acetamino, butyramino or a phenoxybutyramino e.g. 2,4-di-t-amylphenoxybutyramino, and (meth) acryloylamino.

The yellow-forming colour coupler residue may be derived e.g. from colour couplers of the type described in U.S. Pat. Nos. 3,056,675; 3,369,899; 3,393,040; 3,393,041; 3,409,439; 3,619,190; 3,645,742; 3,660,095 and 3,725,072, in Belgian Pat. No. 717,841, and in the published German patent application Nos. 2,002,378; 2,114,576; 2,114,577 and 2,114,578.

The yellow-forming 2-equivalent colour couplers according to the present invention are easy to synthetize, by reaction of the corresponding 2-equivalent couplers having chlorine or bromine as splittable substituent on the active methylene group, with the 2-pyrazolin-5-one compound in the presence of a base as is illustrated in the preparations hereinafter. The couplers have high coupling activity i.e. the heterocyclic group is easily split off during colour development, which results in high colour densities. They also have high stability in the photographic element during storage and provide less fog than the corresponding generally used 2-equivalent couplers with chlorine as splittable group. Moreover, with the 2-equivalent couplers of the invention dyes can be formed upon colour development, which have better light-stability and less side-absorption than the surrounding chlorine-substituted 2-equivalent couplers.

Representative examples of 2-equivalent yellow-forming colour couplers according to the present invention are illustrated in the following preparations.

Preparation 1

The compound corresponding to the following formula:

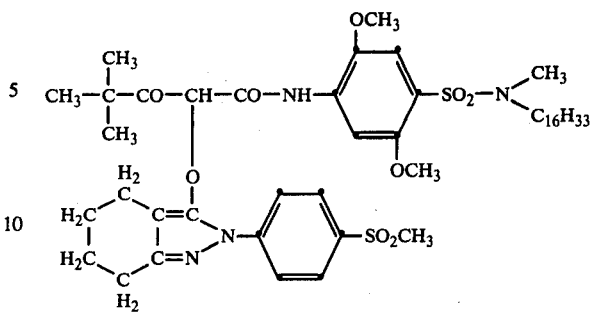

was prepared as follows:

1.44 g of a 55% (by weight) oil dispersion of sodium hydride containing 0.79 g (0.033 mole) of NaH was added while keeping the temperature below 20° C. to a solution of 9.64 g (0.033 mole) of 1-(4-methylsulphonylphenyl)-3,4-tetramethylene-2-pyrazolin-5-one in 60 ml of dry dimethylformamide. After 20 min 18.9 g (0.033 mole) of (α-pivaloyl-α-chloro-[2′,5′-dimethoxy-4′(N-methyl,N-hexadecylsulphamoyl)] acetanilide were added to the first solution. After a reaction time of 1 h at 20° C., the reaction mixture was poured into 400 ml of water containing 10 ml of acetic acid. The residue formed was extracted with dichloromethane and the solution was dried with anhydrous sodium sulphate. After the solvent had been evaporated, the residual oily phase was purified chromatographically. Yield: 16.7 g.

Melting point: approx. 50° C.

Preparation 2

The compound corresponding to the following formula:

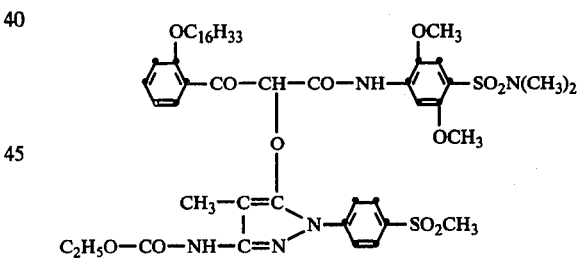

was prepared as follows:

To a suspension of 11.2 g (0.033 mole) of 1-(4-methylsulphonylphenyl)-3-ethoxycarbonylamino-4-methyl-2-pyrazolin-5-one in 60 ml of acetonitrile, 1.44 g of a 55% (by weight) oily sodium hydride dispersion containing 0.033 mole of NaH, was added while cooling was applied. After 20 min a solution was obtained, to which 20.4 g (0.03 mole) of α-(2-hexadecyloxybenzoyl)-α-chloro-[2′,5′-dimethoxy-4′-(N,N-dimethylsulphamoyl)]-acetanilide were added. After having been kept for 5 h at 20° C. the reaction mixture was poured into 500 ml of water containing 10 ml of acetic acid and the residue formed was extracted with dichloromethane. The dried solution was evaporated to dryness and the residue was purified chromatographically.

Yield; 16 g. Melting point: approx. 45° C.

Preparation 3

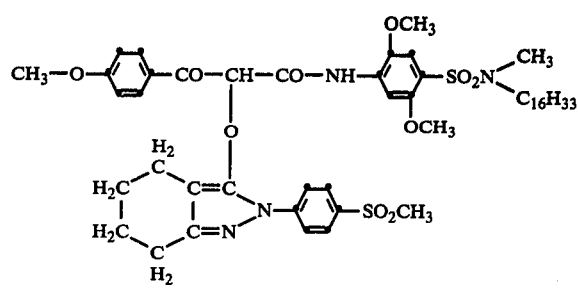

was prepared as follows:

The reaction proceeded as described in preparation 2 with 20.4 g (0.03 mole) of α-(4-methoxybenzoyl)-α-chloro[2′,5′-dimethoxy-4′-(N-methyl-N-hexadecylsulphamoyl)]acetanilide, 9.64 g (0.033 mole) of 1-(4-methylsulphonylphenyl)3,4-tetramethylene-2-pyrazolin-5-one, and 1.44 g (0.033 mole) of a 55% by weight oily dispersion of sodium hydride and 60 ml of dimethylformamide.

The oil obtained was purified chromatographically. Yield: 14 g (50%). Melting point: approx. 50° C.

Preparation 4

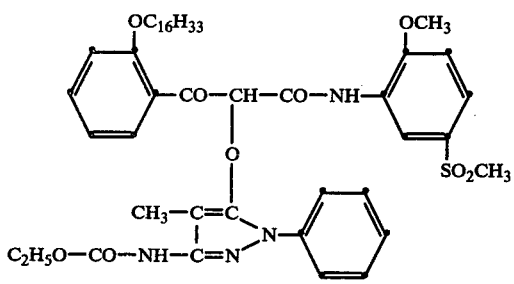

The preparation of the above compound proceeded analogously to that described in preparation 2. The following ingredients were used:

31.1 g (0.05 mole) of α-(o-hexadecyloxybenzoyl)α-chloro(2′-methoxy, 4′-methylsulphonyl) acetanilide 13.1 g (0.05 mole) of 1-phenyl-3-ethoxycarbonylamino-4-methyl-2-pyrazolin-5-one 2.18 g (0.05 mole) of 55% by weight oily dispersion of sodium hydride and 100 ml of dimethylformamide.

After a reaction time of 3 h at 20° C. the reaction mixture was poured into 100 ml of water. The oily phase formed was extracted with dichloromethane. The purification was done chromatographically.

Yield; 14.8 g. Melting point: approx. 50° C.

Preparation 5

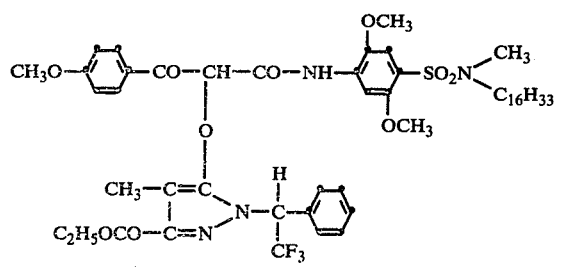

The above compound was prepared by adding to a mixture of 27.2 g (0.04 mole) of α-(4-methoxybenzoyl)-α-chloro-[2′,5′-dimethoxy-4′(N-methyl, N-hexadecylsulphamoyl)]acetanilide and 13.1 g (0.04 mole) of 1(1-phenyl-2,2,2-trifluoroethyl)-3-ethoxycarbonyl-4-methyl-2-pyrazolin-5-one, 80 ml of acetonitrile and 10 ml (0.08 mole) of tetramethylguanidine were added with stirring. The reaction mixture was heated to 35° C. until complete dissolution. After 30 min the reaction mixture was poured into 500 ml of 2N hydrochloride acid. The oily phase formed was extracted with dichloromethane and the solution was dried with anhydrous sodium sulphate. The solvent was evaporated and the oily phase was crystallized from isopropanol.

Yield: 15 g. Melting point: 130° C.

Preparation 6

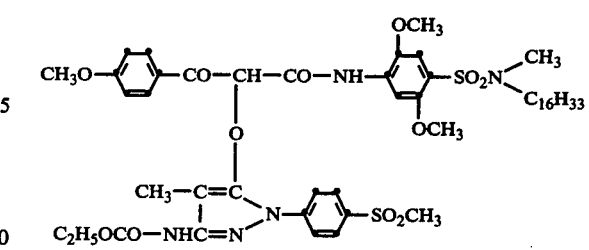

The above compound was prepared as follows: a mixture of 17.4 g (0.051 mole) of 1-(4-methylsulphonylphenyl)-3-ethoxycarbonylamino-4-methyl-2-pyrazolin-5-one, 34.05 g (0.05 mole) of α-(4-methoxybenzoyl)-α-chloro[2′,5′-dimethoxy-4′-(N-methyl-N-hexadecylsulphamoyl)]-acetanilide, and 7.07 g (0.051 mole) of anhydrous potassium carbonate dissolved in 100 ml of dimethylformamide was heated for 30 min at 50° C. The reaction mixture was poured in 1 l of icewater and 10 ml of acetic acid and the residue formed was filtered. This residue was dissolved in dichloromethane, the solvent was dried over anhydrous magnesium sulphate. After filtering off of the drying agent and evaporation of the filtrate, the soft product was stirred in 100 ml of ether and filtered off. The product was recrystallized from ethanol.

Yield: 19.5 g (41%). Melting point: 115° C.

Preparations 7–10

The following products were prepared as described in preparation 2:

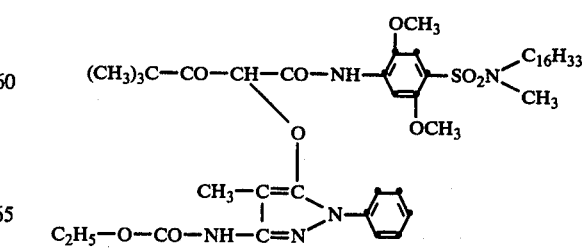

Yield: 27%. Melting point: 71° C.

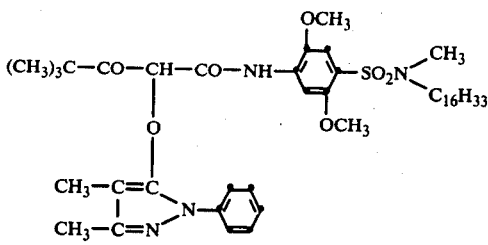

Yield: 58%; yellow oily product.

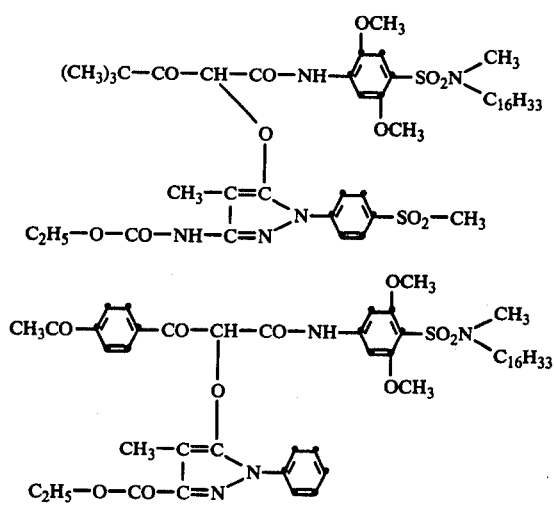

Oily product.

The 2-equivalent colour couplers of the present invention are particularly intended for use in photographic multicolour silver halide materials. As is known in the art, in order to obtain sufficient fastness to diffusion in hydrophilic colloid layers, more particularly a silver halide emulsion layer of the photographic element the colour couplers comprise at least one ballasting group, more particularly a straight-chain or branched-chain alkyl group having at least 5, preferably from 10 to 18 C-atoms e.g. in the substituents $Q^1$, $Q^2$ and $Q^3$ of the above general formula II.

Another method of making the couplers of the invention fast to diffusion in hydrophilic colloid layers e.g. emulsion layers is to use the couplers in polymeric form e.g. by copolymerisation of acylacetanilide monomeric couplers according to the invention comprising in the benzoyl, or preferably in the anilide portion more particularly the 5-position an ethylenic group of the formula:

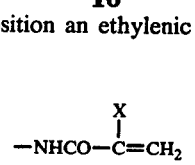

wherein X is hydrogen, halogen, $C_1$-$C_5$ alkyl, e.g. methyl, aralkyl or aryl, with one or more non-dye forming monomers comprising at least one ethylenic group e.g. acrylates, methacrylates, acrylic acid, methacrylic acid, acrylamides, methylacrylamides, etc. The polymeric couplers are preferably prepared by emulsion polymerisation techniques e.g. as described in Belgian Patent Specification No. 669,971 and in United Kingdom patent specification No. 1,130,581. The following preparations are illustrations of monomeric and polymeric couplers according to the invention.

Preparation 11

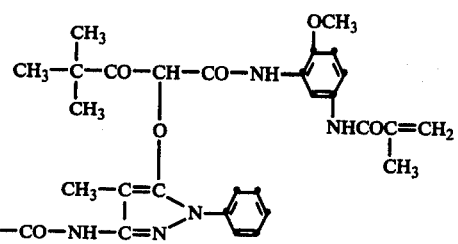

was prepared as follows:

To a solution of 13.05 g (0.05 mole) of 1-phenyl-3-ethoxycarbonylamino-4-methyl-2-pyrazolin-5-one in 100 ml of dimethylformamide and 1 ml of nitrobenzene, 2.7 g (0.0625 mole) of a 55% by weight sodium hydride oily dispersion were added in such a way that the temperature was kept below 20° C. After 15 min 18.3 g (0.05 mole) of α-pivaloyl-α-chloro-(2'-methoxy-5'-methacrylamino)acetanilide were added and the reaction mixture was stirred for 90 min at 20° C.

The mixture was poured into 500 ml of water and 15 ml of acetic acid and the residue formed was filtered off. The residue was stirred in methanol, filtered off and recrystallized from acetonitrile.

Yield: 19 g (64%). Melting point: 187° C.

Preparation 12

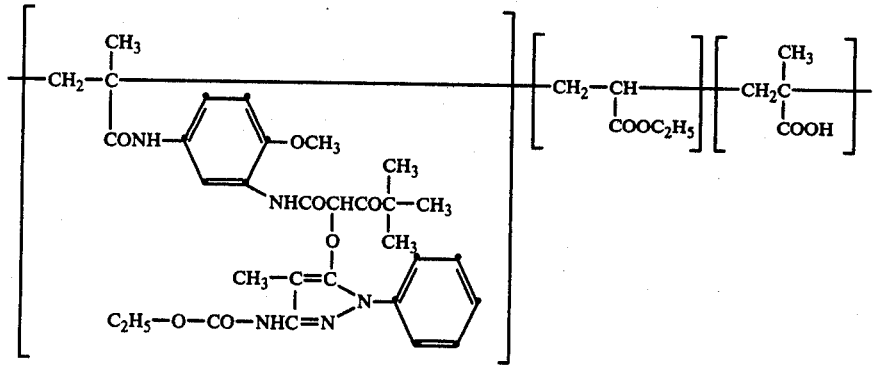

In a reaction vessel fitted with a thermometer, a reflux condenser, and three dropping funnels, 110 ml of demineralized water, in which 1.35 g of sodium oleylmethyltauride had been dissolved, were heated to 95° C.

4.5 ml of an initiator solution (1% by weight aqueous solution of the sodium salt of 4,4'-azo-bis(4-cyano valeric acid) and 1/5 part of an aqueous suspension of the monomer of preparation 6 were added.

The total amount of monomer suspension contains 18 g of the monomer, 0.9 g of the sodium salt of oleylmethyltauride, and 45 ml of demineralized water. The suspension was obtained by mere stirring of the above-mentioned ingredients.

By the addition of 5.4 g of a mixture consisting of equal parts by weight of methacrylic acid and ethyl acrylate the temperature fell to 84°–86° C. After a few minutes polymerization started and the temperature was raised to 96° C. As soon as this temperature was reached, initiator solution, monomer dispersion, and liquid mixture of comonomers were added again in the same amounts as described above. After an initial temperature drop to 88° C. heating was started again up to 96° C. The addition of the ingredients was repeated three times. Subsequently there was heated for 45 min up to reflux temperature. The latex obtained was cooled to 20° C. and filtered.

Yield: 197 g of latex.

The amount of solids per 100 ml of latex was 13.1 g. The amount of polymer per 100 ml of latex was 11.8 g. The equivalent molecular weight is 1894.

Although the invention is particularly concerned with non-diffusible colour couplers for use in the photographic element, the 2-equivalent colour couplers according to the invention can also be of the diffusible type for use in developer solutions.

The present invention thus provides a method of producing photographic colour images by exposure and development with an aromatic primary amino colour developing agent of a photographic silver halide material wherein development occurs in the presence of a 2-equivalent colour coupler as defined herein.

The present invention also provides a photographic material comprising at least one silver halide emulsion layer and a 2-equivalent colour coupler as defined herein.

In photographic colour elements, the colour couplers are preferably incorporated into a silver halide emulsion layer but they may also be used in a hydrophilic colloid layer in water-permeable relationship with the emulsion layer.

The colour couplers can be incorporated into hydrophilic colloid compositions according to any of the prior art methods for incorporating photographic ingredients in hydrophilic colloid media. Colour couplers comprising water-solubilizing groups e.g. carboxyl groups and sulpho groups (in acid or salt form) can be incorporated in hydrophilic colloid media from aqueous solutions. Water-insoluble or sparingly water-soluble colour couplers can be incorporated in hydrophilic colloid media from solutions in water-miscible or water-immiscible, high-boiling or low-boiling organic solvents or mixtures thereof preferably in the presence of one or more surface-active agents. After having dispersed the solutions in the hydrophilic colloid medium, the low-boiling water-immiscible solvents are removed. The hydrophilic colloid medium into which the colour couplers are dispersed or dissolved need not necessarily be the coating composition of the specific hydrophilic colloid layer of the photographic element. They can be mere aqueous solutions of hydrophilic colloids, e.g. gelatin, which can be stored as such and incorporated into the coating composition of the specific layer just before coating.

The colour couplers according to the present invention that do not comprise water-solubilizing groups have high solubility in water-immiscible high-boiling and low-boiling organic solvents and therefore are preferably incorporated from such solutions in hydrophilic colloid media.

For this purpose the colour couplers are dissolved in a water-immiscible low-boiling solvent e.g. ethyl acetate, methylene chloride, diethyl carbonate, chloroform, etc. and/or in a water-immiscible high-boiling solvent e.g. di-n-butylphthalate, tricresyl phosphate or a polyhalogenocarbonateacetal of the type described in the published German Pat. Appl. No. 2,613,504 and the solutions are dispersed in extremely fine droplets, preferably in the presence of one or more wetting or dispersing agents into the hydrophilic colloid medium e.g. aqueous gelatin, or into water, the low-boiling sparingly water-miscible solvent then being removed by evaporation. The stable dispersion of the colour couplers can be stored as such and then admixed whenever desired with the coating composition itself of the hydrophilic colloid layer such as a silver halide emulsion layer into which the compounds are intended to be present.

More details about particularly suitable techniques that may be employed for incorporating the colour couplers of the invention into a hydrophilic colloid layer of a photographic material can be found in U.S. Pat. Nos. 2,269,158; 2,284,887; 2,304,939; 2,304,940 and 2,322,027; United Kingdom patent specification Nos. 791,219; 1,098,594; 1,099,414; 1,099,415; 1,099,416; 1,099,417; 1,218,190; 1,272,561; 1,297,347 and 1,297,947, French Pat. No. 1,555,663, Belgian Pat. No. 722,026, German Pat. No. 1,127,714, and the published German Pat. No. 2,613,504.

The couplers according to the invention may be used in conjunction with various kinds of photographic emulsions. Various silver salts may be used as the sensitive salt such as silver bromide, silver iodide, silver chloride or mixed silver halides such as silver chlorobromide, silver chloroiodide, silver bromoiodide and silver chlorobromoiodide. The couplers can be used in emulsions of the mixed packet type as described in U.S. Pat. No. 2,698,794 or emulsions of the mixed grain type as described in U.S. Pat. No. 2,592,243. The colour couplers can be used with emulsions wherein latent images are formed predominantly on the surface of the silver halide crystal, or with emulsions wherein latent images are formed predominantly inside the silver halide crystal. They can also be used in diffusion transfer processes and elements.

The hydrophilic colloid used as the vehicle for the silver halide may be e.g., gelatin, colloidal albumin, zein, casein, a cellulose derivative, a synthetic hydrophilic colloid such as polyvinyl alcohol, poly-N-vinylpyrrolidone, etc. If desired, compatible mixtures of two or more of these colloids may be employed for dispersing the silver halide.

The light-sensitive silver halide emulsions of use in the preparation of a photographic material according to the present invention may be chemically as well as optically sensitized. They may be chemically sensitized by effecting the ripening in the presence of small amounts of sulphur-containing compounds such as allyl thiocyanate, allylthiourea, sodium thiosulphate, etc. The emulsions may also be sensitized by means of reductors e.g. tin compounds as described in French Pat.

No. 1,146,955 and in Belgian Pat. No. 568,687, iminoaminomethane sulphinic acid compounds as described in United Kingdom patent specification No. 789,823 and small amounts of noble metal compounds such as gold, platinum, palladium, iridium, ruthenium and rhodium compounds. Chemical sensitization by means of noble metal compounds has been described by R. Koslowsky, Z. Wiss. Photogr. Photophys. Photochem., Vol. 46 (1951), 65–72.

The said emulsions may also comprise compounds that sensitize the emulsions by development acceleration e.g. compounds of the polyoxyalkylene type such as alkylene oxide condensation products as described among others in U.S. Pat. Nos. 2,531,832; 2,533,990; 3,210,191 and 3,158,484; in United Kingdom patent specification Nos. 920,637 and 991,608 and in Belgian Pat. No. 648,710, onium derivatives of amino-N-oxides as described in United Kingdom patent specification No. 1,121,696, compounds of the type described in U.S. Pat. Nos. 3,523,796; 3,523,797; 3,552,968; 3,746,545 and 3,749,574; thioether compounds as described in the published German Pat. Nos. 2,360,878 2,601,778; 2,601,779 and 2,601,814, in U.S. Pat. Nos. 3,046,129; 3,046,132; 3,046,133; 3,046,134, 3,046,135 and 3,201,242, in United Kingdom patent specification Nos. 931,018 and 1,249,248 and in French Pat. No. 1,351,410.

Further, the emulsions may comprise antifoggants, stabilizers e.g. heterocyclic nitrogen-containing thioxo compounds such as benzothiazoline-2-thione and 1-phenyl-2-tetrazoline-5-thione and compounds of the hydroxytriazolopyrimidine type (cfr. Birr, Z. Wiss. Photogr. Photophys. Photochem., Vol. 47 (1952), 2–58). They can also be stabilized with mercury compounds such as the mercury compounds described in Belgian Pat. Nos. 524,121; 677,337 and 707,386 and in U.S. Pat. No. 3,179,520. Other suitable antifoggants for use in colour emulsions comprising the colour couplers of the invention are the aromatic disulphides as described in United Kingdom patent specification No. 1,328,806 and the nitrobenzene compounds of the type described in Belgian Pat. No. 788,687.

The light-sensitive emulsion layers and adjacent layers may comprise any other kind of ingredients such as plasticizers, hardening agents, wetting agents, etc. Examples of suitable hardening agents are formaldehyde, halogen-substituted aldehydes containing a carboxyl group e.g. mucobromic and mucochloric acid, diketones, dialdehydes, methane sulphonic acid esters, etc., halogen substituted triazine e.g. 2,4-dichloro-6-hydroxy-s-triazine, carbodiimines as described in U.S. Pat. Nos. 2,938,892 and 3,098,693, dihydroquinolines as described in published German patent application (DT-OS) No. 2,332,317, carbamoylpyrimidinium as described in published German patent application (DT-OS) Nos. 2,225,230 and 2,317,677 and carbamoyloxypyrimidiniums as described in published German patent application (DT-OS) No. 2,408,814.

The non-diffusing colour couplers described in the present invention are usually incorporated into one of the differently spectrally sensitive silver halide emulsion layers of a photographic multilayer colour material, which includes positive, negative and reversal material. Such photographic multilayer colour material usually comprises a support, a red-sensitized silver halide emulsion layer with a cyan-forming colour coupler, a green-sensitized silver halide emulsion layer with a magenta-forming colour coupler and a blue-sensitive silver halide emulsion layer with a yellow-forming colour coupler.

These colour materials may further comprise one or more intermediate layers, filter layers and protective surface layers. The multilayer photographic element may comprise for the formation of each of the three colour separation images more than one, e.g. two, silver halide emulsion layers of different sensitivity and comprising the same or different colour couplers including 2-equivalent and/or 4-equivalent colour couplers e.g. the undermost silver halide emulsion layer being of lower sensitivity. These layers may comprise colour couplers of different coupling activity for the formation of the same colour separation image as described in published German patent application (DT-OS) No. 1,958,702. The photographic element may comprise one or more free competing couplers to improve colour reproduction by colourless coupling with oxidized developer agent in areas where these oxidation products should be renderend ineffective. Suitable competing couplers have been described in United Kingdom patent specification Nos. 861,138 and 914,145 and in the published German Pat. Nos. 1,909,067 and 2,304,319. They may be present in silver halide emulsion layers or in intermediate and surface coatings.

The differently spectrally sensitive silver halide emulsions of multilayer photographic colour elements may be spectrally sensitized by methods well known in the art.

The emulsions comprising the yellow-forming colour couplers of the invention are usually not sensitized spectrally. Their inherent sensitivity for the blue region of the spectrum is usually sufficient. However, it is possible to spectrally sensitize the emulsions for the bleu region of the spectrum e.g. by means of sensitizing dyes as described in United Kingdom patent specification Nos. 1,285,078 and 1,293,543. The photographic elements containing the yellow colour couplers of the present invention may comprise in the same or adjacent emulsion layer other yellow forming 2-equivalent or 4-equivalent yellow forming couplers. The elements may further comprise masking compounds e.g. couplers containing at the coupling position phenylazogroups which are split off upon colour development as well as known D.I.R.-couplers which upon colour development split off development inhibiting compounds (e.g. as described in U.S. Pat. Nos. 3,227,551 and 3,632,345. They may also comprise in the layer containing the yellow forming couplers of the invention or in adjacent layers D.I.R.-compounds which do not form dyes e.g. hydroquinone derivatives as described in U.S. Pat. Nos. 3,379,529; 3,620,746; 3,632,345 and 3,639,417 and other D.I.R. compounds e.g. of the type as described in published German patent application (DT-OS) No. 2,502,892.

The emulsions can be coated on a wide variety of photographic emulsion supports. Typical supports include cellulose ester film, polyvinylacetal film, polystyrene film, polyethylene terephthalate film and related films or resinous materials, as well as paper and glass. It is also possible to employ paper coated with α-olefin polymers e.g. paper coated with polyethylene, polypropylene, ethylene-butylene copolymers, etc.

For the production of photographic colour images according to the present invention an exposed silver halide emulsion layer is developed with an aromatic primary amino developing substance in the presence of a colour coupler according to the present invention. All colour developing agents capable of forming azomethine dyes can be utilised as developers. Suitable developing agents are aromatic compounds such as p-phenylenediamine and derivatives for example N,N-diethyl-p-phenylenediamine, N-butyl-N-sulphobutyl-p-phenylenediamine, 2-amino-5-diethylaminotoluene, 4-amino-N-ethyl-N(β-methanesulphonamidoethyl)-m-toluidine, N-hydroxyethyl-N-ethyl-p-phenylenediamine, 4-amino-3-methyl-N-ethyl-N(β-hydroxyethyl)-aniline sulphate, etc.

The developing compositions may comprise the usual ingredients as well as development activating compounds including polyoxyethylene compounds, onium compounds and organic thioethers as referred to hereinbefore, antifoggants e.g. nitrobenzene compounds of the type described in the Belgian Pat. No. 788,687, etc.

The following examples illustrate the present invention.

EXAMPLE 1

The colour couplers listed in the following table were incorporated into a conventional silver iodobromide (2.3 mole % iodide) emulsion in an amount of about 0.006 mole of coupler per mole of silver halide.

The couplers were incorporated from aqueous gelatin dispersions obtained by dissolving the couplers in ethyl acetate, dispersing the solution in aqueous gelatin and removing the ethylacetate by evaporation under reduced pressure.

The emulsion portions were coated on a conventional film support, dried and overcoated with a gelatin antistress layer. After having been dried, the emulsions were exposed through a step-wedge and processed as follows.

The materials were developed for 8 min. at 20° C. in a developing bath of the following composition:

| | |
|---|---|
| N,N-diethyl-p-phenylene diamine sulphate | 2.75 g |
| hydroxylamine sulphate | 1.2 g |
| sodium hexametaphosphate | 4 g |
| anhydrous sodium sulphite | 2 g |
| anhydrous potassium carbonate | 75 g |
| potassium bromide | 2.5 g |
| water to make | 1 liter |

The developed materials were treated for 2 min. at 18°–20° C. in an intermediate bath comprising 30 g of sodium sulphate in 1 liter of water.

The materials were rinsed for 15 min. with water and treated in a bleach bath of the following composition:

| | |
|---|---|
| borax | 20 g |
| potassium bromide | 15 g |
| anhydrous potassium bisulphate | 4.2 g |

Yellow coloured wedge images were obtained which as is apparent from the results listed in the following table have superior light-stability as compared with the corresponding 2-equivalent couplers with known splittable substituent and as compared with the parent 4-equivalent coupler.

| Coupler | Percentage density loss* at density D=0.5 | at density D=1.5 |
|---|---|---|
| coupler of prep. 2 | 30 | 15 |
| parent 4-equivalent coupler | 60 | 28 |
| corresponding 2-equivalent coupler with methyl carbonyl phenoxy as splittable group | 38 | 29 |
| coupler of prep. 3 | 34 | 20 |
| parent 4-equivalent coupler | 42 | 25 |
| corresponding 2-equivalent coupler with p-methoxy carbonyl phenoxy as splittable group | 54 | 39 |

*loss in density on a percentage basis of the yellow wedges measured at density 0.5 and 1.5, after having been exposed for 15 h to 1500 Watt Xenon lamp in a xenotest 150 apparatus of "Original Hanau-Quartzlampen G.m.b.H." Hanau am Main, Germany.

EXAMPLE 2

Superior light-stability was also obtained when exposing and colour processing materials as described in example 1 using other conventional processing solutions based on the developing agents listed in the following table.

| Coupler | Developing agent | Percentage density loss* at Density 0.5 | at Density 1.5 |
|---|---|---|---|
| coupler of preparation 2 | 2-amino-5-diethylamino toluene hydrochloride | 24 | 16 |
| parent 4-equivalent coupler | " | 60 | 25 |
| corresponding 2-equivalent coupler with methyl carbonyl phenoxy as splittable group | " | 40 | 29 |
| coupler of preparation 2 | 2-amino-5[N-ethyl-N-(β-methylsulphonylamino)ethyl]aminotoluene sulphate | 14 | 12 |
| parent 4-equivalent coupler | " | 56 | 18 |
| corresponding 2-equivalent coupler with methyl carbonyl phenoxy as splittable group | " | 32 | 25 |
| coupler of preparation 2 | 4-amino-3-methyl-N-ethyl-N(β-hydroxyethyl)aniline sulphate | 18 | 16 |
| corresponding 2-equivalent coupler with methyl carbonyl phenoxy as splittable group | " | 56 | 35 |
| coupler of preparation 3 | 2-amino-5-diethylamino toluene hydrochloride | 34 | 23 |
| corresponding 2-equivalent coupler with p-methoxycarbonyl-phenoxy as splittable group | " | 42 | 27 |
| coupler of preparation 3 | 2-amino-5[N-ethyl-N-(β-methylsulphonylamino)ethyl]aminotoluene sulphate | 22 | 15 |
| parent 4-equivalent coupler | " | 32 | 14 |
| corresponding 2-equivalent coupler with methoxycarbonyl-phenoxy as splittable group | " | 38 | 23 |
| coupler of preparation 3 | 4-amino-3-methyl-N-ethyl-N(β-hydroxyethyl) aniline sulphate | 24 | 19 |
| parent 4-equivalent coupler | " | 42 | 17 |
| corresponding 2-equivalent coupler with methoxycarbonyl-phenoxy as splittable group | " | 44 | 25 |
| coupler of preparation 4 | 2-amino-5-diethylamino toluene hydrochloride | 26 | 11 |
| parent 4-equivalent | | | |

-continued

| Coupler | Developing agent | Percentage density loss* at Density 0.5 | at Density 1.5 |
|---|---|---|---|
| coupler | " | 36 | 18 |
| coupler of preparation 4 | 2-amino-5[N-ethyl-N-β-methylsulphonylamino) ethyl]amino toluene sulphate | 14 | 10 |
| parent 4-equivalent coupler | " | 28 | 16 |
| coupler of preparation 1 | 2-amino-5-diethylamino toluene hydrochloride | 28 | 19 |
| parent 4-equivalent coupler | " | 42 | 25 |
| coupler of preparation 1 | 4-amino-3-methyl-N-ethyl-N(β-hydroxyethyl) aniline sulphate | 14 | 14 |
| parent 4-equivalent coupler | " | 34 | 28 |

We claim:

1. A photographic material comprising at least one silver halide emulsion layer and a 2-equivalent colour coupler for yellow which corresponds to the formula

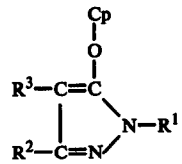

wherein:
Cp represents a pivaloyl acetanilide or benzoylacetanilide yellow forming colour coupler residue which is capable of oxidative coupling with an aromatic primary amino developing agent and which is linked to the 5-pyrazolyl-oxy group at its coupling position,
R¹ represents an alkyl group or an aryl group,
R² represents an alkyl group, an aryl group, a carboxyl, an alkoxycarbonyl or an amino group,
R³ an alkyl group, or
R² and R³ together represent a tri- or tetramethylene group, forming with the carbon atoms to which they are attached a 5- or 6-membered carboxylic ring,
and wherein the 5-pyrazolyloxy group is split off during oxidative coupling with an aromatic primary amine colour developer and forms a competing coupler molecule, which is capable of coupling with the oxidation products of an aromatic primary amino colour developer to form a colourless compound.

2. A photographic material according to claim 1, wherein the pivaloyl acetanilide or benzoylacetanilide colour coupler residue corresponds to one of the following formulae III or IV:

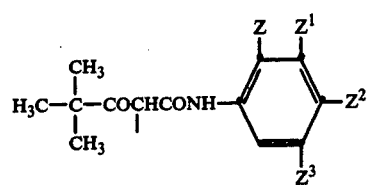

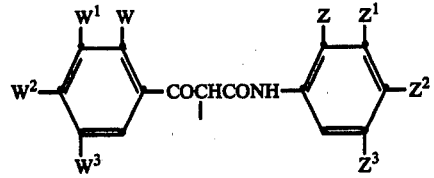

wherein:
Z represents halogen, an alkyl group, an alkoxy group, an aryloxy group or a N-substituted amino group,
each of Z¹, Z² and Z³, which may be the same or different represents hydrogen, halogen, an alkyl group, an alkoxy group, an aryl group, an aryloxy group, an alkoxycarbonyl group, an aryloxycarbonyl group, an alkylamino group, an arylamino group, an alkylsulphonyl group, a carbamoyl group, a sulphamoyl group, an acylamino group, an ureido group, hydroxy, a sulpho or a carboxy group in acid or salt form, and
each of W, W¹, W² and W³, which may be the same or different represents hydrogen, an alkyl group, an alkoxy group, an aryloxy group, halogen, an amino group.

3. A photographic material according to claim 1, wherein the 5-pyrazolyl group is selected from the group consisting of:

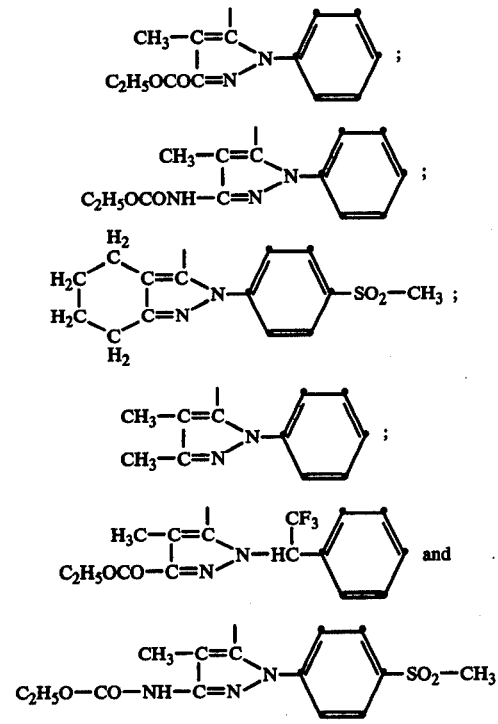

4. A photographic material according to claim 1, wherein the colour coupler is present in a silver halide emulsion layer.

5. Method of producing a coloured photographic image in a photographic light-sensitive silver halide material, which comprises exposing the material and developing it with an aromatic primary amino colour developing agent in the presence of a 2-equivalent colour coupler for yellow which corresponds to the formula

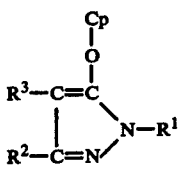

wherein:
Cp represents a pivaloyl acetanilide or benzoylacetanilide yellow forming colour coupler residue which is capable of oxidative coupling with an aromatic primary amino developing agent and which is linked to the 5-pyrazolyl-oxy group at its coupling position, $R^1$ represents an alkyl group or an aryl group, $R^2$ represents an alkyl group, an aryl group, a carboxyl, an alkoxycarbonyl or an amino group, $R^3$ an alkyl group, or $R^2$ and $R^3$ together represent a tri- or tetramethylene group, forming with the carbon atoms to which they are attached a 5- or 6-membered carboxylic ring, and wherein the 5-pyrazolyloxy group is split off during oxidative coupling with an aromatic primary amine colour developer and forms a competing coupler molecule, which is capable of coupling with the oxidation products of an aromatic primary amino colour developer to form a colourless compound.

* * * * *